United States Patent [19]

Propst

[11] Patent Number: 4,843,868
[45] Date of Patent: * Jul. 4, 1989

[54] CEMENT MIX ANALYZING SYSTEM

[76] Inventor: Robert L. Propst, 18845 NE. 49th Pl., Redmond, Wash. 98052

[*] Notice: The portion of the term of this patent subsequent to May 3, 2005 has been disclaimed.

[21] Appl. No.: 175,748

[22] Filed: Mar. 31, 1988

Related U.S. Application Data

[63] Continuation of Ser. No. 940,036, Dec. 10, 1986, Pat. No. 4,741,201.

[51] Int. Cl.$^4$ .............................................. G01N 33/38
[52] U.S. Cl. .................................................. 73/61 R
[58] Field of Search ................. 73/61 R, 866, 863.23, 73/54

[56] References Cited

U.S. PATENT DOCUMENTS

| | | | |
|---|---|---|---|
| 2,264,223 | 11/1941 | Stancliffe | 73/866 X |
| 3,499,328 | 3/1970 | Kenny et al. | 73/866 |
| 3,863,494 | 2/1975 | Nasser | 73/54 |
| 4,144,762 | 3/1979 | Duxbury | 73/866 |
| 4,432,674 | 2/1984 | Klose et al. | 73/863.23 X |
| 4,615,215 | 10/1986 | Sugimoto et al. | 73/61 R X |

FOREIGN PATENT DOCUMENTS

504970 2/1976 U.S.S.R. ............................. 73/61 R

Primary Examiner—Stewart J. Levy
Assistant Examiner—Joseph W. Roskos
Attorney, Agent, or Firm—Seed and Berry

[57] ABSTRACT

A method for sampling cement and determining the cement-to-water ratio includes use of a device having an elongated, hollow probe for insertion into a batch of cement mix. The probe has an aggregate separator at one end and a chamber at the other end. A manually actuated piston subjects the chamber to a vacuum to draw the cement mix through the aggregate separator and through a sand collector into the chamber. A hydrophilic cement filter surrounds the chamber with a hydroscopic filter surrounding the hydrophilic filter. As the sample is drawn into the chamber, it passes through the hydrophilic filter into the hydroscopic filter. The weights of the collected cement and water are then determined after taking into account the original weight of the filters.

2 Claims, 6 Drawing Sheets

CEMENT MIX ANALYZING SYSTEM

This application is a continuation of U.S. patent application Ser. No. 940,036, filed Dec. 10, 1986 now U.S. Pat. No. 4,741,201.

DESCRIPTION

1. Technical Field

The present invention relates to a system for quickly determining the cement-to-water ratio of a cement mix preparatory to pouring at a job site.

2. Background Art

At the present time there is a need for a practical means of determining the cement-to-water ratio in a cement mix at the critical time just before it is poured on the job. Laboratory tests have been developed, but they take at least one-half hour to complete in a laboratory environment and are thus normally not practical for field testing of concrete mixes. As a result of the lack of on-the-job determination of the cement-to-water ratio, there is a tendency to overdesign concrete structures to give an additional safety factor to allow for variances from the cement-to-water ratio specification. This adds unnecessary expense to the concrete structure.

Furthermore, if the cement-to-water ratio in the cement mix used on a job does not meet specifications, the result may be a structure with an undetected hazardous strength deficiency or one which must be replaced or strengthened by structural addition before final inspection approval can be achieved on the job. Thus, six groups have a vital interest in having a means for accurate determination of the cement-to-water ratio in a mix before the pour: (1) the designer of the structure; (2) the structural engineers specifying the mix; (3) the supplier of the concrete mix; (4) the contractor using the mix; (5) the inspection personnel; and (6) the owner of the structure.

DISCLOSURE OF THE INVENTION

The present invention aims to provide an improved method and apparatus for determining the cement-to-water ratio of a cement mix in a manner meeting the following performance criteria:

1. Takes a short time to complete a field test;
2. Allows sampling of the mix in the cement delivery truck without running out a batch;
3. Provides preservable evidence of the test;
4. Is a durable, reliable, portable unit with easy field-maintenance qualities;
5. Low cost per test; and
6. Is a clean, dry process requiring no field water or wash-up or field power sources.

In practicing the present invention, the first step involves obtaining a sample of a concrete mix batch and screening out the aggregate. To the sample is added a fixed amount of wetting agent which then assists in passing the aggregate-free sample through a series of filtering screens to remove the sand and fines, thereby providing a sample which is substantially only an aqueous solution with cement in suspension. In this state, the sample is subjected to a hydrophilic unit which filters out cement particles and a hygroscopic unit which absorbs the liquid passed through the hydrophilic unit. This action continues until the hygroscopic unit is saturated. At this point, the passing-through action ceases and, consequently, any further deposit of cement ceases on the surface of the hydrophilic filter.

The hydrophilic filter with the cement deposit thereon is then removed from the test chamber and weighed. A heavier bag mix will have deposited more cement on the filter than a lesser bag mix. A proper calibration translates this figure into a water-to-cement ratio or bag mix determination.

BEST MODE FOR CARRYING OUT THE INVENTION

Referring to FIGS. 1–11, the preferred embodiment of the present invention includes a disposable sampling unit 20 which fits within a guard tube 22 mounted on one end of a foldable handle assembly 24 having a vacuum unit 26 at its other end. The sampling unit 20 has an outer cylindrical shell 28 containing a series of filtering elements progressing from an entry unit 30, which has a cylindrical neck 30a extending upwardly into the shell 28 from an annular shoulder 30b. Projecting axially into the neck 30a is a cylindrical cartridge holder 30c which is supported at its lower end by a set of radial ribs 30d extending downwardly from the shoulder 30b. These ribs 30d are rounded at their lower ends and have screening vanes 30e therebetween which are close enough together to block the passage of coarse aggregate; hence, the entry unit 30 functions as a first stage filter. At its upper end, the cartridge holder 30c has an inturned stop lip 30f against which a wetting agent cartridge 32 seats.

Figure 1:
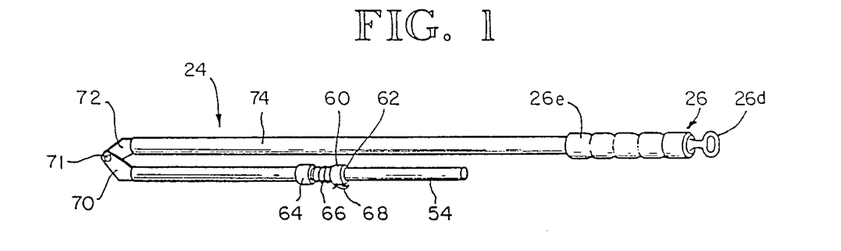
FIG. 1 is a side elevational view of a handle assembly, shown in folded position, to be used with a guard tube and sampling unit in accordance with the present invention.
Figure 2:
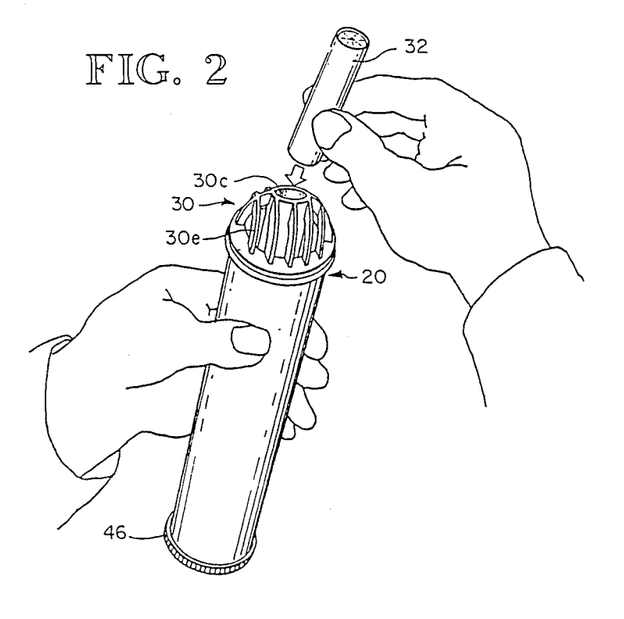
FIG. 2 is a perspective view of the sampling unit.
Figure 3:
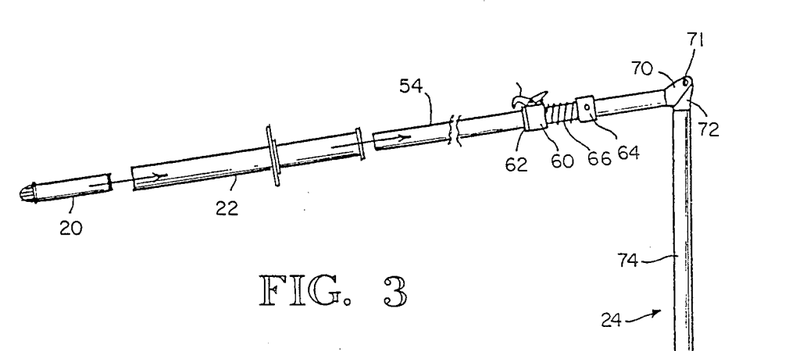
FIG. 3 is a side elevational view of the handle assembly in operative position and showing the guard tube and sampling unit ready to be combined with the handle assembly into a sampling assembly, as indicated by the direction arrows.
Figures 4, 5, 6:
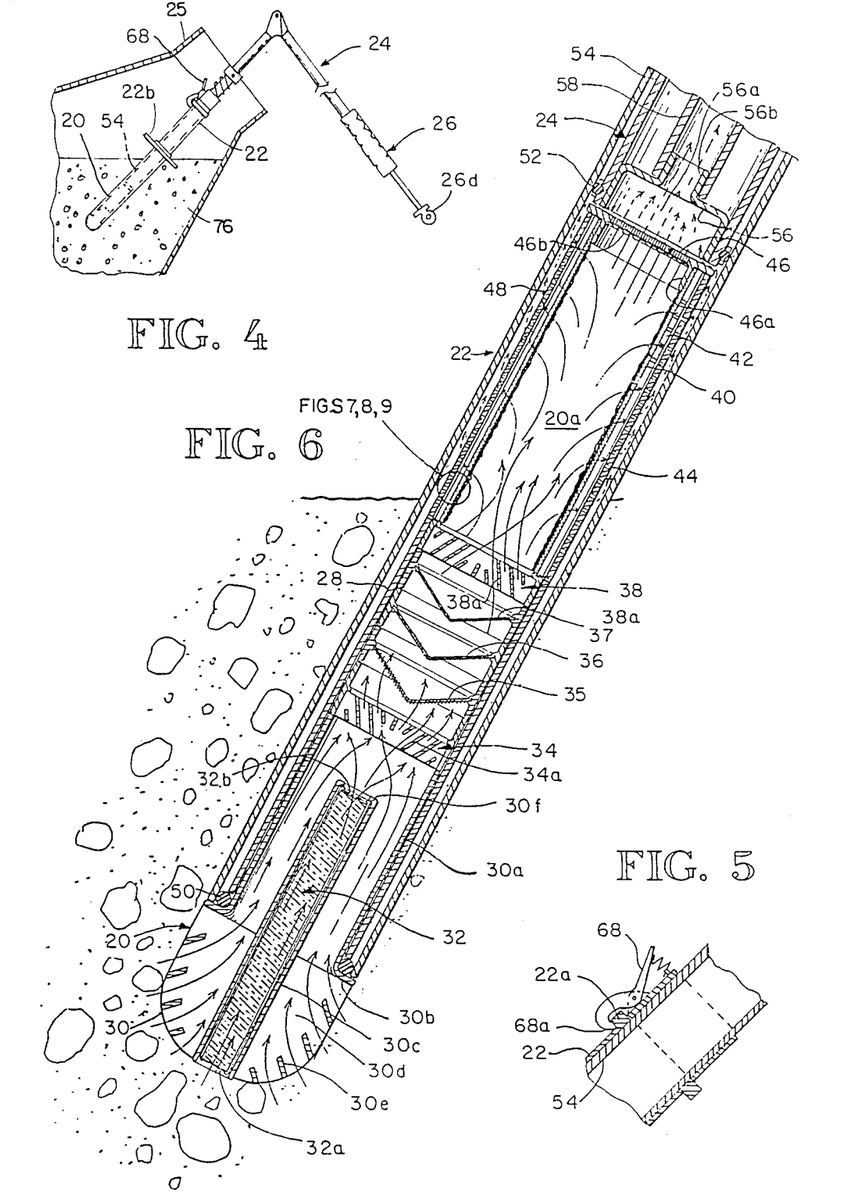
FIG. 4 is a side elevational view showing the sampling assembly in operative position taking a sample.
FIG. 5 is a detail longitudinal sectional view illustrating the connection of the guard tube with the handle assembly.
FIG. 6 is a longitudinal vertical sectional view through the sampling unit when in operative position with the guard tube and handle assembly.

Above the entry unit 30, the shell 28 contains in consecutive order a bottom mixing unit 34, a series of conical screen units 35–37, and a central mixing unit 38. The mixing units 34, 38 have respective mixing vanes 34a, 38a projecting radially inward from respective outer rings 34b, 38b. The vanes 34a are sloped so as to direct upwardly flowing material outwardly, whereas the vanes 38a are sloped to direct the material inwardly. The screen units 35–37 provide three progressively finer screening stages so as to filter out fine aggregate, sand, and fines, respectively.

Above the central mixing unit 38, there is provided, in concentric relation, an inner hydrophilic filter 40, a central hygroscopic unit 42, and an outer air-permeable liquid barrier 44 surrounding a test chamber 20a. Surmounting the upper end of the shell 28 is a cap 46 which has an annular neck extension 46a to which an upper end portion of the hydrophilic filter 40 is detachably connected by a suitable pressure-sensitive adhesive. The cap 46 has central perforated portion covered with an air-permeable water barrier 46b.

The barrier 44 may be an extension of the shell 28 or a liner in the shell, in which case the portion of the shell 28 surrounding the barrier would be perforated. In either instance, the passage of air is permitted into a concentric chamber 48 between the shell 28 and the guard tube 22. This chamber 48 is closed at its lower end by an elastomeric O-ring 50 and at its upper end by an elastomeric O-ring 52 which extends between the guard tube 22 and a mounting tube 54 provided by the handle assembly 24. The lower end of the mounting tube 54 is radially ported above the cap 46 and below the O-ring 52 to connect the chamber 48 with a vacuum chamber 56a established by an insert 56 which fits into the lower end of the mounting tube 54 and is formed with an upper nipple 56b onto which a flexible vacuum hose 58 is secured. This vacuum hose 58 extends axially along the handle assembly 24 to the vacuum unit 26.

The mounting tube 54 has a slide collar 60 thereon which is axially movable between a lower stop ring 62 and an upper stop collar 64 which are fixed to the mounting tube 54. A compression spring 66 is sleeved on the mounting tube 54 between the slide collar 60 and the stop collar 64. To hold the guard tube 22 in position on the mounting tube 54, a spring-loaded latch 68 is provided having a catch finger 68a fitting over a terminal lip 22a at the upper end of the guard tube 22. In the alternative, the catch finger 68a can be pointed to impinge sufficiently on the upper end portion of the guard tube 22 as to hold it in position, thereby making it unnecessary to provide the lip 22a.

Figures 9, 10, 11:
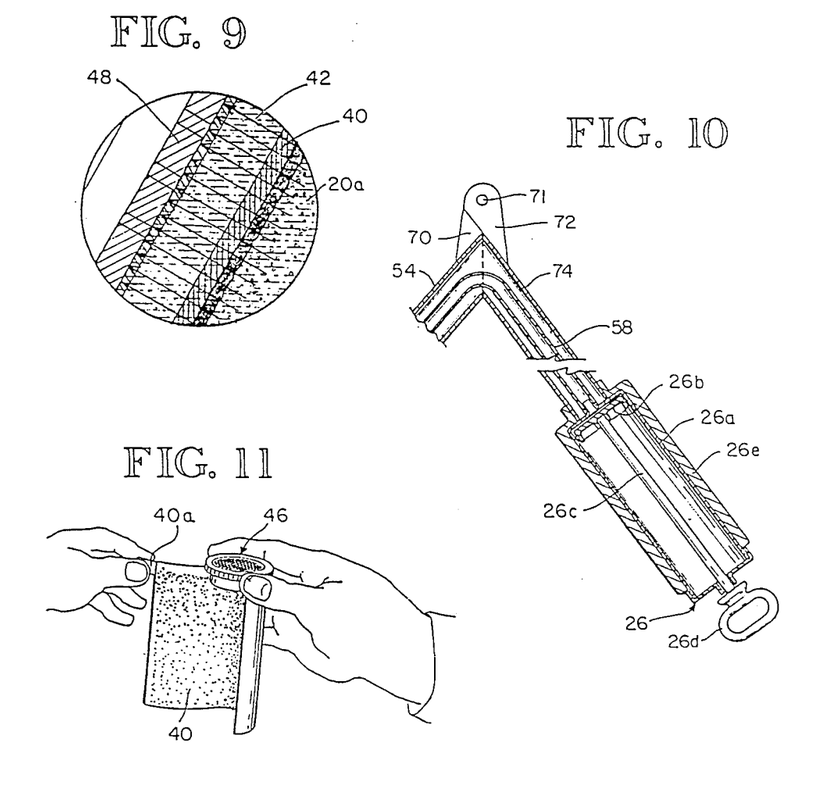
FIG. 10 is a fragmentary longitudinal sectional view of the handle assembly with the piston in the vacuum cylinder portion thereof shown in position ready to take a sample.
FIG. 11 is a perspective view illustrating the step of removing a sample from the sampling unit.

Referring to FIG. 10, at its upper end, the mounting tube 54 has a hinge fitting 70 which is connected by a pivot pin 71 to a complementing hinge fitting 72, in turn mounted on the end of a tubular reach arm 74. This reach arm 74 is connected at its other end to one end of a vacuum cylinder 26a to which the vacuum hose 58 is connected. The vacuum cylinder 26a has a piston 26b working therein which is connected to a piston rod 26c extending through the opposite end of the cylinder to a handle 26d. Surrounding the vacuum cylinder is a hand grip 26e.

Preparatory to using the probe, the guard tube 22 is sleeved onto the mounting tube 54, and the handle 26d is pushed toward the hand grip 26e until the piston 26b reaches the far end of the vacuum cylinder 26a. Then a sampling unit is inserted in the guard tube 22 with a cartridge 32 of wetting agent in the cartridge holder 30c. The wetting agent is confined in this cartridge by frangible end membranes 32a, 32b. The sample taker then manipulates the handle assembly to insert the sampling unit 20 and guard tube 22 into a concrete batch which is ready for pouring. Typically, this will be done by manipulating the probe through the fill neck 75 of the rotating drum on a cement delivery truck, as indicated in FIG. 4. The articulation of the probe handle assists in this manipulation and enables a sample taker standing on the ground to push the head of the probe into the mix 76, preferably to a depth beyond the screen units 35–37. The guard tube 22 allows the unit to be inserted to a sufficient depth without getting cement on the handle assembly 24. In this regard, it is preferred to provide the guard tube with a stop collar 22b for engaging the top surface of the cement 76 in the mix truck to give the person taking the sample an indication of when adequate sampling depth has been made.

Figure 7:
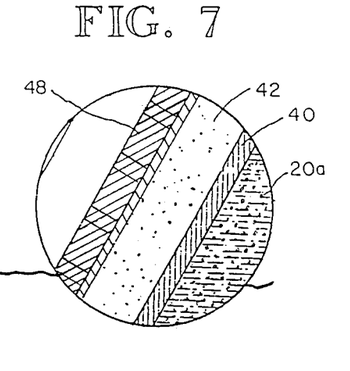
FIGS. 7, 8 and 9 are detailed views to an enlarged scale taken as indicated in FIG. 6 and showing respectively, operation at the start of the sample taking, operation during the sample taking, and operation at the conclusion of the sample taking.
Figure 8:
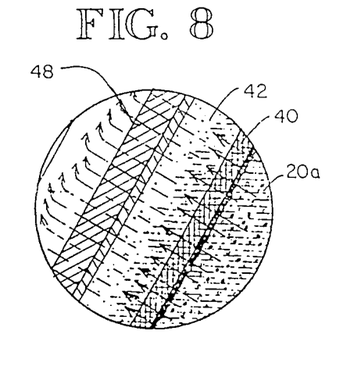

The operator then pulls out the handle 26d with one hand while gripping the hand grip 26e with the other hand so as to draw a vacuum within the sampling unit 20 via the hose 58, vacuum chamber 56a, and air-permeable water barriers 44 and 46b. As a result of this vacuum, a sample of the cement mix is drawn through the entry head unit 30 between the screening vanes 30e, which block passage of the relatively large aggregate into the probe. At the same time, the frangible membranes at the ends of the wetting agent cartridge 32 are ruptured by the vacuum effect so that, as the cement mix sample (with larger aggregate removed) passes the cartridge holder 30c, the wetting agent is drawn into the mix sample to blend therewith before reaching the filtering screens 35–37. This blending is assisted by the action of the bottom mixing unit 34. The screens 35–37 then filter out the sand, and passage therethrough of the mix sample is assisted by the wetting agent. The drawing of the vacuum is continued until the test chamber 20a is filled with a charge of filtered cement mix and the hygroscopic unit 44 is saturated with water and wetting agent. Radial passage of water and wetting agent beyond the hygroscopic unit 44 is prevented by the air-permeable barrier 44, and upward axial passage of water and wetting agent from the test chamber 20a is blocked by the air-permeable water barrier 46b. The operator then withdraws the probe from the cement mix.

Figure 12:
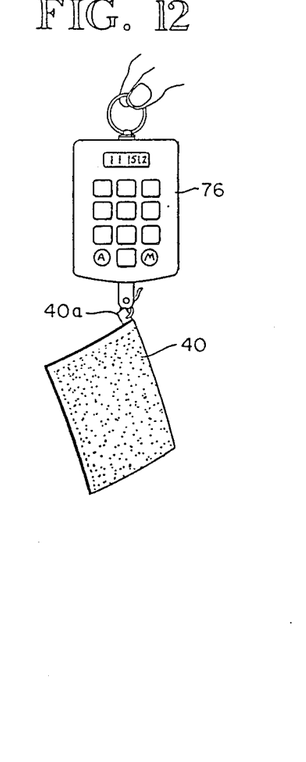
FIG. 12 illustrates the step of weighing a sample.
Figure 13:
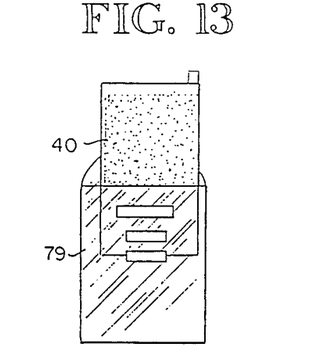
FIG. 13 illustrates the step of storing a sample.

The sampling unit 20 can then be removed from within the guard tube 22 by pushing the slide collar 60 toward the upper stop collar 64 so as to move the guard tube 22 upwardly relative to the sampling unit 20 along the mounting tube 54. Then the cap 46, with the cement-coated hydrophilic filter 40 attached thereto, is gripped and withdrawn from the rest of the sampling unit 20, whereupon the filter 40 is stripped from the cap 46 by use of a pull-tab 40a. The cement-coated filter 40 is then clipped to a scale/calculator 76 and weighed. The determined weight reflects a combination of the dry weight of the filter 40, the weight of the cement collected by the filter 40, and the dry weight of the water and wetting agent retained by the filter 40 and collected cement. If the cement mix contains an additive to the cement, the determined sample weight will also reflect the effect of the additive on the collected cement/additive on the filter 40 and the water/wetting agent retained thereby.

The weight of water/wetting agent retained by the cement (or cement/additive) will be directly proportional to the amount of water/wetting agent collected, and the combined weight of the filter 40 and water/wetting agent retained by the filter 40 will be constant. Hence, if the constant representing the combined weight of the filter 40 and water/wetting agent normally retained thereby is subtracted from the determined weight of the sample, the resulting difference is directly proportional to the amount of cement (or cement/additive) collected by the filter 40. Furthermore, since the amount of water/wetting agent required to saturate the hygroscopic unit 42 is constant, the amount of cement (or cement/additive) collected by the filter 40 while the hygroscopic unit 42 is being saturated will be constant for a given cement or cement/additive mix. Accordingly, if the scale/calculator is programmed to automatically subtract the constant representing the combined weight of the hydrophilic filter 40 and water/wetting agent normally retained thereby from the weight of the weighed sample, the calculated result (the weight of cement or cement/additive plus water/wetting agent retained thereby) will always accurately reflect the cement (or cement/ additive) to water ratio of the sampled cement/additive mix. The scale/calculator can also be programmed to multiply the aforesaid calculated result by the constant percentage of dry cement (or cement/additive) in wetted cement (or cement/additive) and to then divide this multiplication product by the sum of (a) the constant weight of the water/wetting agent required to saturate the hygroscopic unit 42, (b) the constant weight of water/wetting agent retained by the hydrophilic filter 40, and (c) the amount of water/wetting agent in the collected wetted cement (or cement/additive) determined by multiplying the combined weight of cement (or cement/additive) plus water/wetting agent retained thereby, by the constant percentage of water/wetting agent in wetted cement (or cement/additive).

It is recognized that the specific gravity of the wetting agent may be slightly different from that of water, but the difference, if any, is so small as to be insignificant in the results achieved by the invention or required by the normal field test. The purpose of the test is to determine whether the cement (or cement/additive)-to-water ratio in a mix at the job site is within a reasonable tolerance of the specified ratio. The present invention achieves a test accuracy well within accepted tolerances.

A permanent record of the field test performed in the described manner can be achieved by depositing the weighed hydrophilic filter from the test in a flat poly envelope which is marked with suitable identification.

If the mix being tested is beginning to gel (set up), and hence should be judged unsuitable to pour, the hydrophilic filter will be starved of cement deposit during the test because of the inability of the water to separate from the cement and migrate into the hydroscopic unit. In such an instance, the sample will weigh light, thereby indicating that the mix is unsuitable.

Figure 14:
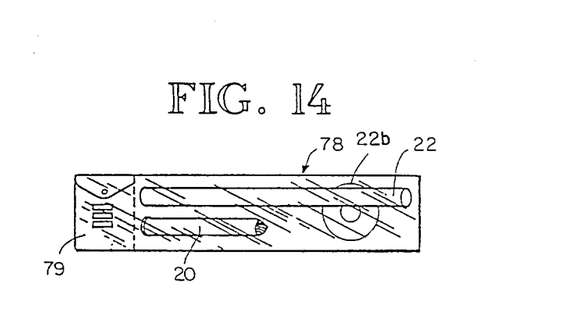
FIG. 14 is a front view of a packet in which sampling components are stored.
Figure 15:
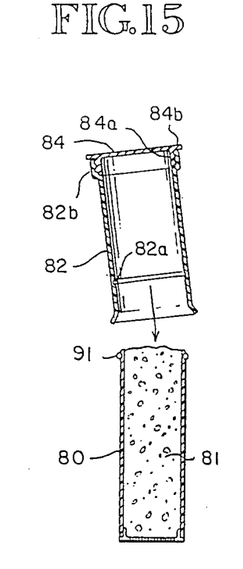
FIGS. 15 through 20 are vertical sectional views illustrating the steps of using a second embodiment of the invention.
Figure 16:
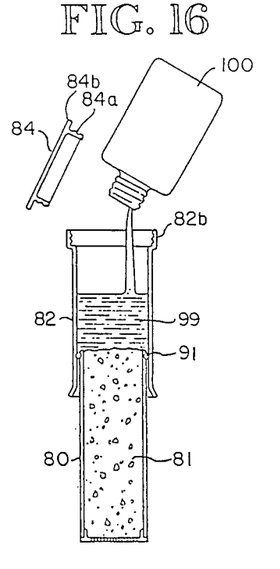
Figure 17:
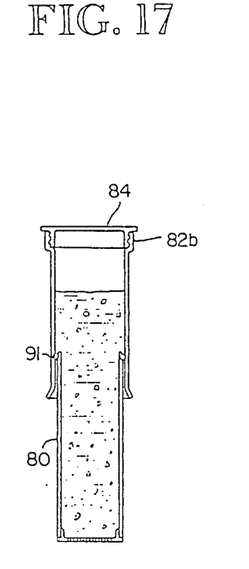
Figure 18:
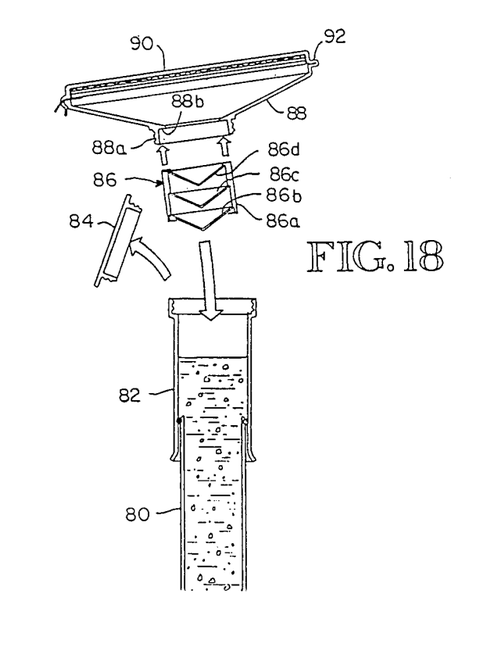
Figure 19:
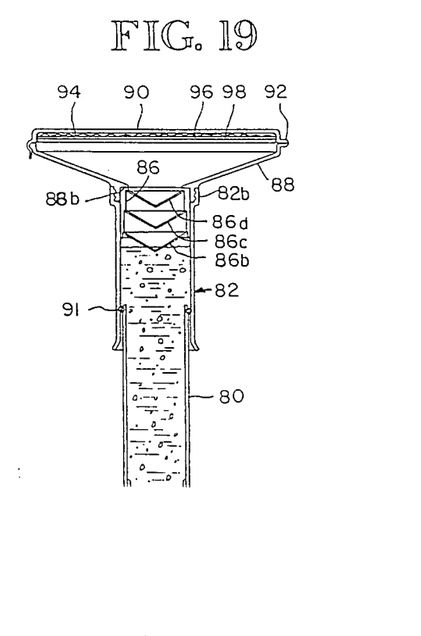
Figure 20:
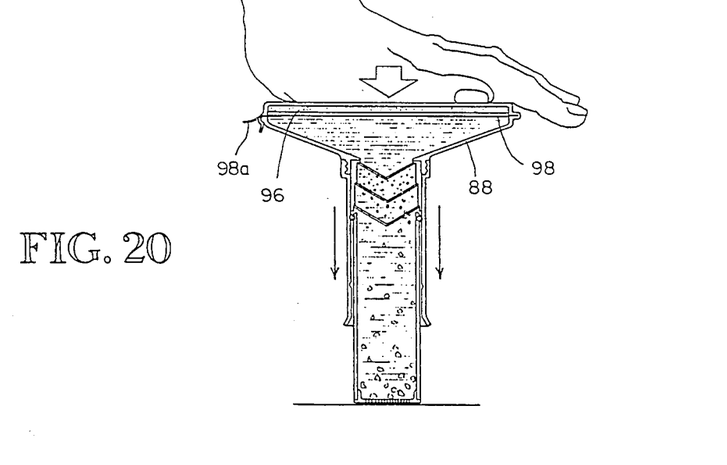

The disposable test apparatus to be used in accordance with the invention can be conveniently provided as a test sample kit 78 within a disposable test package envelope and comprises the sampling unit 20 (without wetting agent), the guard tube 22, and a test specimen envelope 79. Cartridges 32 of wetting agent may be provided in a suitable package. At the conclusion of the test, the guard tube 22 is released and removed from the mounting tube 54; and the guard tube, together with the used sampling unit 20 and cap 46, can be placed in the test package envelope for disposal without subjecting the sample taker to contact with cement present on the lower portion of the guard tube and on the entry head 30. When the guard tube 22 is removed, the handle unit is free of cement and folds as a compact unit for easy transport and storage.

A second embodiment of the apparatus for practicing the present invention is shown in FIGS. 15–20. Referring thereto, it is seen that there is provided a cylindrical container 80 for a concrete mix sample 81, an extension sleeve 82, a screw cover 84, a filter unit 86, and a frustoconical dome 88 with a hinged lid 90.

The container 80 has an O-ring seal 91 near the top which is adapted to fit into an internal groove 82a in the sleeve 82 when the sleeve is fitted over the container 80. The sleeve 82 is flared at its lower end for ease of insertion over the upper end of the container 80, and has an enlarged upper end portion 80b which is internally threaded to receive external threads on a neck 84a of the cap 84. The rim portion 84b of the cap 84 preferably extends radially beyond the upper end portion 84b of the container for ease in manually gripping it for application or removal.

The screen unit 86 has a holding ring 86a which is adapted to fit within the extension 82 and is internally stepped to provide a three downwardly facing annular shoulders against which three screens 86b, c, and d are seated. These screens are preferably conical for greater surface area, and are of decreasing mesh size from bottom to top so as to progressively remove light aggregate, sand, and fines.

The dome 88 has a bottom neck 88a which is externally threaded to register with the internal threads on the enlarged upper end portion of the extension 82, and which is adapted to fit over the holding ring 86a. An internal annular stop shoulder 88b is provided at the top of the neck 88a to engage the upper end of the screen unit 86. At its enlarged upper end, the dome 88 has an integral hinge connection 92 with the lid 90. Vent holes 90a are provided in the lid 90 for passage of air through an airpermeable water barrier 94 applied on the underside or top surface of the lid, and the lid has a depending spring catch 90b adapted to snap fit over a protuberance 88c on the dome 88. Detachably fitting into the underside of the lid is an upper hydroscopic unit 96 and a lower hydrophilic filter 98 which preferably has a peripheral tab 98a for manual gripping.

In the use of the apparatus of the second embodiment, a sample 81 of the wet cement mix to be tested is placed in the container 80. Preferably, this sample has been preliminarily screened to the extent that the larger aggregate has been removed. This screening of the larger aggregate can be performed as the sample is being drawn in the same general manner as previously described with reference to the screening vanes 30e at the probe head.

With the sample 81 in the container 82, the extension 82 is applied to the container to the extent that the O-ring 91 fits within the groove 82a. Then, wetting agent 99 is poured into the extension 82, preferably from a disposable container 100 of predetermined capacity. Next, the cover 84 is screwed into position and the wetting agent and sample 81 are blended together by manually shaking the container 80, extension 82, and cover 84 as a shaker unit. Following this blending, the cover 84 is removed, the screen unit 86 is introduced to the upper end of the extension 82, and the dome 88 is threaded into the enlarged upper end portion 82b after the lid 90 has been fitted with a hygroscopic unit 96 and a hydrophilic filter 98 has been applied covering the underside of the hygroscopic unit and having its tab 98a projecting outwardly from beneath the rim of the lid 90.

The next step comprises manually pushing down on the lid 90, with the container 80 resting on a support surface so that the extension 82 telescopes downwardly over the container 80 and the cement mix/wetting agent is responsively forced upwardly through the screens 86b–d into the interior of the dome 88, thereby providing in the dome chamber a thoroughly screened sample containing cement (or cement/additive) and water/wetting agent. Continued manual pressure on the lid 90 causes the water/wetting agent in the sample material in the dome to be forced through the hydrophilic unit 96 into the hygroscopic unit 96 until the latter is saturated. As a result, the cement (or cement/additive) which had been suspended in the water/wetting agent now contained in the hygroscopic unit 96 and hydrophilic filter 98 is collected on the surface of the latter. The lid 90 is then swung open and the hydrophilic filter 98 with the cement (or cement/additive) collected thereon is removed for weighing and calculation, as previously described.

In the accompanying claims, it is intended that the word "cement" be interpreted as being purely cement or a combination of cement with an additive or additives, and that the word "sand" be interpreted as being small aggregate, sand, and fines.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. In a method for determining the cement-to-liquid ratio in a sample of a cement and liquid mix, the steps of:
   passing the sample through a hydrophilic collector unit of predetermined weight which is adapted to filter out the cement in the sample;
   continuously collecting the liquid passing through the hydrophilic collector unit in a hydroscopic collector unit of predetermined weight; and
   determining the weights of the collected cement and liquid.

2. In a method for determining the cement-to-liquid ratio in a sample of a cement and liquid mix, the steps of:
   passing the sample through a generally cylindrical hydrophilic collector unit of predetermined weight which is adapted to filter out the cement in the sample;
   collecting the liquid passing through the hydrophilic collector unit in a hydroscopic collector unit of predetermined weight which surrounds said hydrophilic collector unit; and
   determining the weights of the collected cement and liquid.

* * * * *